(12) United States Patent
Park et al.

(10) Patent No.: US 9,359,401 B2
(45) Date of Patent: Jun. 7, 2016

(54) PEPTIDE ANALOGUES WITH AN EXCELLENT MOISTURIZING EFFECT AND USE THEREOF

(75) Inventors: Kee-Don Park, Daejeon (KR); Chae-Jin Lim, Daejeon (KR); Seok-Jeong Yoon, Daejeon (KR); Seon-Deok Kwon, Daejeon (KR)

(73) Assignee: INCOSPHARM CORPORATION, Daejeon (KR)

( * ) Notice: Subject to any disclaimer, the term of this patent is extended or adjusted under 35 U.S.C. 154(b) by 0 days.

(21) Appl. No.: 14/119,854

(22) PCT Filed: May 22, 2012

(86) PCT No.: PCT/KR2012/004029
§ 371 (c)(1),
(2), (4) Date: Nov. 22, 2013

(87) PCT Pub. No.: WO2012/161497
PCT Pub. Date: Nov. 29, 2012

(65) Prior Publication Data
US 2014/0113868 A1    Apr. 24, 2014

(30) Foreign Application Priority Data
May 23, 2011  (KR) .................. 10-2011-0048722

(51) Int. Cl.
| | |
|---|---|
| A61K 8/64 | (2006.01) |
| A61K 38/05 | (2006.01) |
| A61K 38/06 | (2006.01) |
| A61K 38/07 | (2006.01) |
| C07K 5/072 | (2006.01) |
| C07K 5/093 | (2006.01) |
| C07K 5/113 | (2006.01) |
| C07K 5/11 | (2006.01) |
| C07K 14/00 | (2006.01) |
| A61Q 19/00 | (2006.01) |
| A61Q 5/00 | (2006.01) |
| A61Q 19/08 | (2006.01) |
| C07K 5/068 | (2006.01) |

(52) U.S. Cl.
CPC ............... *C07K 5/1019* (2013.01); *A61K 8/64* (2013.01); *A61K 38/05* (2013.01); *A61K 38/06* (2013.01); *A61K 38/07* (2013.01); *A61Q 5/00* (2013.01); *A61Q 19/00* (2013.01); *A61Q 19/08* (2013.01); *C07K 5/06086* (2013.01); *C07K 5/06104* (2013.01); *C07K 5/0819* (2013.01); *C07K 5/1021* (2013.01); *C07K 14/001* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 4,032,676 | A | 6/1977 | Heins et al. |
| 4,518,614 | A | 5/1985 | Parkinson |
| 7,671,009 | B2 | 3/2010 | Ludin et al. |
| 2002/0182237 | A1 | 12/2002 | Bissett et al. |
| 2004/0192649 | A1 | 9/2004 | Bissett et al. |
| 2004/0241114 | A1 | 12/2004 | Gupta |
| 2005/0065090 | A1 | 3/2005 | Ludin et al. |
| 2006/0188462 | A1 | 8/2006 | Bissett et al. |
| 2006/0188467 | A1 | 8/2006 | Bissett et al. |
| 2006/0193809 | A1 | 8/2006 | Bissett et al. |
| 2007/0053858 | A1 | 3/2007 | Tanner et al. |
| 2008/0025932 | A1 | 1/2008 | Bissett et al. |
| 2008/0032990 | A1* | 2/2008 | Khalifah et al. ......... 514/252.18 |
| 2009/0099098 | A1* | 4/2009 | Khavinson et al. ............ 514/18 |
| 2010/0261902 | A1* | 10/2010 | Xu et al. ........................... 546/5 |
| 2011/0045036 | A1 | 2/2011 | Lintner et al. |

FOREIGN PATENT DOCUMENTS

| | | | |
|---|---|---|---|
| CA | 2465123 | A1 | 5/2003 |
| CH | 689373 | A5 | 3/1999 |
| FR | 2944446 | A1 | 10/2010 |
| FR | 2944527 | A1 | 10/2010 |
| GB | 1464000 | A | 2/1977 |
| JP | 50-95201 | A | 7/1975 |
| JP | 2004-238386 | A | 8/2004 |
| JP | 2005-503335 | A | 2/2005 |
| JP | 2006-502077 | A | 1/2006 |
| JP | 2010-105980 | A | 5/2010 |
| KR | 10-2002-0096607 | A | 12/2002 |
| KR | 10-2004-0083584 | A | 10/2004 |
| KR | 10-2005-0015177 | A | 2/2005 |
| KR | 10-0652122 | B1 | 11/2006 |
| KR | 10-0847299 | B1 | 7/2008 |
| KR | 10-2010-0025430 | A | 3/2010 |
| WO | WO-84/01710 | A1 | 5/1984 |
| WO | WO-2010/082176 | A2 | 7/2010 |

OTHER PUBLICATIONS

Padamwar et al.: "Silk sericin as a moisturizer: an in vivo study", Journal of Cosmetic Dermatology, 2005, pp. 250-257, vol. 4.
Sothornvit, "Extracted sericin from silk waste for film formation," Songklanakarjn J. Sci. Technol., Jan.-Feb. 2010, 32(1), pp. 17-22.

* cited by examiner

*Primary Examiner* — Jeffrey E Russel
(74) *Attorney, Agent, or Firm* — McDermott, Will & Emery LLP (57) ABSTRACT

The present invention relates to a peptide analog or a pharmaceutically acceptable salt thereof with excellent moisturizing effect, and use thereof for moisturization. More specifically, the present invention relates to a novel peptide analog or a pharmaceutically acceptable salt thereof, a method for preparation thereof, a moisturizing cosmetic composition comprising the same as an active ingredient, and a pharmaceutical composition for prevention and treatment of xeroderma.

12 Claims, 2 Drawing Sheets

PEPTIDE ANALOGUES WITH AN EXCELLENT MOISTURIZING EFFECT AND USE THEREOF

TECHNICAL FIELD

The present invention relates to a peptide analogue or a pharmaceutically acceptable salt thereof with excellent moisturizing effect, and use thereof for moisturization. More specifically, the present invention relates to a novel peptide analogue or a pharmaceutically acceptable salt thereof, a method for preparation thereof, a moisturizing cosmetic composition comprising the same as an active ingredient, and a pharmaceutical composition for prevention and treatment of xeroderma.

BACKGROUND ART

From the medical point, skin performs a function as a protection film at the outermost part of human body, and performs important functions for preventing loss of body ingredients such as water, electrolyte, and the like, and simultaneously blocking inflow of external harmful substances. Particularly, stratum corneum forms the outermost layer of skin to prevent moisture loss inside of skin from dry external environment, and simultaneously, it holds appropriate moisture and exhibits flexibility and elasticity.

In the stratum corneum of normal skin, 10% or more of moisture is commonly contained to afford elasticity and flexibility. The degree of moisture content decreases from dermis to epidermis. Stratum corneum consists of about 15% water, 70% protein and 15% lipid, while dermis, particularly keratinocyte consists of 70% water, 15% protein and 5% lipid. As the keratinocyte approaches to the surface, moisture content gradually decreases, and finally reaches to 5~10%. The outermost part of skin, even if the skin is very good, does not contain 20% or more of water. The moisture content of stratum corneum of moist skin is commonly around 15%.

However, skin loses water balance due to various factors including external environments such as aging, change in hormone secretion, wind, temperature and sun, and the like, and physical factors such as wash and shave, and the like, and it easily becomes dry skin with moisture content of 10% or less. Thus, skin loses elasticity and flexibility, and eventually, skin protection function disappears to induce skin fissure, erythema, pruritus, and the like, and more worse, generate skin disease such as psoriasis, atopic dermatitis, and the like.

To solve these problems, it may be ideal to solve causative factors, but since the causes are various and mostly uncontrollable, the second-best solution is being considered. It may include a method of blocking water evaporation of skin cells to prevent decrease in skin moisture content, and a method of minimizing irritation from external environment by forming an artificial moisturization film on the skin. Among them, a method of forming an artificial moisturization film is most simple, and for this, various kinds of skin moisturizers and moisturizing cosmetics are being developed.

However, skin friendly materials that are conventionally used as raw materials of moisturizer and moisturizing cosmetics have various problems. For example, although polyhydric alcohols such as glycerin or sorbitol that are mostly used as moisturizer ingredients exhibit excellent moisturizing effect, they cause serious stickiness to induce displeasure, and they are easily separated on the skin surface due to physical influences and thus long-lasting effects cannot be expected. And, raw materials such as propyleneglycol, 1,3-butyleneglycol may cause side effects to skin such as erythema, when repeatedly used in a large amount. Moreover, natural moisturizing factors (NMF) of Na-lactate, sodium pyrrolidone carboxylic acid (PCA-Na), urea, and the like have strong electrolytic property, and thus, they have problems of damaging emulsion stability of cosmetics or moisturizer, and the like, and the effects are limited.

Recently, there are increasing efforts to form a moisturization film on the skin using biological materials or biomaterials instead of chemical materials. Among them, there are many efforts to use natural extracts, various proteins and decomposition products thereof as moisturizing ingredients, and practically, products containing these ingredients have been developed and are commercially available. As the protein decomposition product, collagen decomposition product, elastin decomposition product, silk decomposition product, and the like are mainly used. However, they do not exhibit constant moisturizing effects, and they should be contained in high concentrations to achieve moisturizing effects because the effects are slight.

Particularly, silk which is protein-based fiber consisting of fibroin and sericin has been mainly used as cloth in the past, but recently, it has been found through the studies that silk protein and its decomposition products, peptides and amino acids have the effects for lowering blood cholesterol concentration, relieving hangovers, and preventing dementia, and thus, it draws attentions as health functional foods and cosmetics. And, it has been disclosed in various patents and papers that silk-derived protein and its decomposition product, silk peptide posses moisturizing effects and thus may be used as cosmetics.

Specifically, Korean Registered Patent No. 10-0428431 discloses use of decomposition product of silk protein by proteinase (low molecular weight silk protein), Korean Registered Patent No. 10-0652122 discloses use of hydrolysis product of sericin, Korean Patent Application No. 10-2003-0053873 and Korean Patent Application No. 10-2003-0018086 disclose use of sericin protein, and Journal of Cosmetic Dermatology, 2005, 4:250-257 mentions the possibility of using sericin protein as moisturizer. However, these articles only mention sericin and its decomposition product among silk protein, and the results are mostly for moisturizing effects limited for a short time, and thus, in practical use, sufficient moisturizing effect cannot be obtained.

And, Korean Registered Patent No. 10-0847299 discloses use of specific silk peptide fragments that have increased moisturizing effects by removing interference of fragments without moisturizing effects among the decomposition products of fibroin protein. However, according to the process of obtaining decomposition products, the yields and the moisturizing effects of the final products may be varied, and when applied for a cosmetic formulation, moisture retention time may not exceed 8 hours, and thus, there is a demand for performance improvement.

DISCLOSURE

Technical Problem

Accordingly, as the result of efforts to overcome the above problems and develop a moisturizer with long-lasting excellent moisturizing effect, the inventors synthesized peptide analogues of a novel concept comprising only functional groups with excellent moisturizing effect from the fragments of the decomposition product of fibroin protein among the decomposition product of silk protein, investigated excellent moisturizing effects of these peptide analogues, and completed the present invention.

Technical Solution

It is an object of the invention to provide a novel peptide analogue or a pharmaceutically acceptable salt thereof with excellent moisturizing effect.

It is another object of the invention to provide a method for preparing the peptide analogue or the pharmaceutically acceptable salt thereof.

It is still another object of the invention to provide a moisturizing cosmetic composition comprising the peptide analogue or the pharmaceutically acceptable salt thereof.

It is still another object of the invention to provide a pharmaceutical composition for prevention or treatment of xeroderma comprising the peptide analogue or the pharmaceutically acceptable salt thereof.

It is still another object of the invention to provide a method for moisturizing skin, comprising administering the peptide analogue or the pharmaceutically acceptable salt thereof to an individual.

It is still another object of the invention to provide a method for treating xeroderma, comprising administering the peptide analogue or the pharmaceutically acceptable salt thereof to an individual.

Advantageous Effects

The peptide analogues with excellent moisturizing effect according to the present invention may maintain optimum moisturization state of skin without side effects such as skin irritation when applied to human body, thus anticipating improvement of skin state from skin problems due to dryness and inhibition of skin worsening, and it may be very useful in the industrial fields of external medicine, manufacture of cosmetics, and the like.

And, a moisturizing composition comprising the peptide analogues with excellent moisturizing effect according to the present invention may manifest excellent effect for improving moisture retention capacity of skin, and has good applicability and spreadability when applied to skin. The skin moisturizing composition comprising peptide analogues with excellent moisturizing effect does not cause side effect and stickyness to skin, and forms a long lasting moisturizing film on the skin surface, and thus, it may manifest effects for improvement of skin roughness and prevention of skin aging, and the like.

MODE FOR INVENTION

According to one embodiment, the present invention relates to a novel peptide analogue and a pharmaceutically acceptable salt thereof with excellent moisturizing effect.

Specifically, the present invention relates to the peptide analogue having the following Chemical Formula 1 or the pharmaceutically acceptable salt thereof:

[Chemical Formula 1]

wherein, $X_1$, $X_2$, $Y_1$ and $Y_2$ are the same or different, and independently represents —H, —$(CH_2)_mC(=O)OH$, or a W group having the following Structural Formula, wherein $R_1$, $R_2$, $R_3$ and $R_4$ are the same or different, and independently represents —H or —$(CH_2)_mC(=O)OH$, $Z_1$ is O and $Z_2$ is H, or $Z_1$ is —NHCHRC(=O)OH having an amino acid side chain (R) and $Z_2$ is —NHCHR'C(=O)OH having an amino acid side chain (R') and $Z_1$ and $Z_2$ are amide bonded to each other, n is an integer of 3 to 7, and m is an integer of 1 to 5.

According to preferable embodiment, the present invention relates to a peptide analogue or a pharmaceutically acceptable salt thereof having a structure of the following Chemical Formula 2.

[Chemical Formula 2]

wherein, R and R' are the same or different, and independently represents an amino acid side chain selected from the group consisting of alanine, aspartic acid, glutamic acid, glycine, histidine, lysine, asparagine, glutamine, arginine, tryptophan and tyrosine, n is an integer of 3 to 7, and m is an integer of 1 to 5.

More specifically, the peptide analogue of the Chemical Formula 2 may be preferably a tripeptide wherein aspartic acid, glutamic acid, arginine, histidine or lysine is amide bonded to N-alkylated lysine or N-alkylated ornithine, and specific examples thereof may include (N-alkylated lysine)-aspartic acid-glutamic acid, (N-alkylated lysine)-aspartic acid-arginine, (N-alkylated lysine)-aspartic acid-histidine, (N-alkylated lysine)-aspartic acid-lysine, (N-alkylated lysine)-glutamic acid-arginine, (N-alkylated lysine)- glutamic acid-histidine, (N-alkylated lysine)-glutamic acid-lysine, (N-alkylated lysine)-arginine-histidine, (N-alkylated lysine)-arginine-lysine, (N-alkylated lysine)-histidine-lysine, (N-alkylated ornithine)-aspartic acid-glutamic acid, (N-alkylated ornithine)-aspartic acid-arginine, (N-alkylated ornithine)-aspartic acid-histidine, (N-alkylated ornithine)-aspartic acid-lysine, (N-alkylated ornithine)-glutamic acid-arginine, (N-alkylated)-glutamic acid-histidine, (N-alkylated)-glutamic acid-lysine, (N-alkylated ornithine)-arginine-histidine, (N-alkylated ornithine)-arginine-lysine, and (N-alkylated ornithine)-histidine-lysine (wherein "-" denotes an amide bond).

According to another preferable embodiment, the present invention relates to a peptide analogue or a pharmaceutically acceptable salt thereof having a structure of the following Chemical Formula 3.

[Chemical Formula 3]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine,
n is an integer of 3 to 7, and
m is an integer of 1 to 5.

More specifically, the peptide analogue of the Chemical Formula 3 may be preferably a tetrapeptide wherein N-alkylated lysine or N-alkylated ornithine independently or simultaneously forms a dipeptide, and aspartic acid, glutamic acid, arginine, histidine or lysine is amide bonded thereto; and specific examples thereof may include (N-alkylated lysine)-(N-alkylated lysine)-aspartic acid-glutamic acid, (N-alkylated lysine)-(N-alkylated lysine)-aspartic acid-arginine, (N-alkylated lysine)-(N-alkylated lysine)-aspartic acid-histidine, (N-alkylated lysine)-(N-alkylated lysine)-aspartic acid-lysine, (N-alkylated lysine)-(N-alkylated lysine)-glutamic acid-arginine, (N-alkylated lysine)-(N-alkylated lysine)-glutamic acid-histidine, (N-alkylated lysine)-(N-alkylated lysine)-glutamic acid-lysine, (N-alkylated lysine)-(N-alkylated lysine)-arginine-histidine, (N-alkylated lysine)-(N-alkylated lysine)-arginine-lysine, (N-alkylated lysine)-(N-alkylated lysine)-histidine-lysine, (N-alkylated ornithine)-(N-alkylated ornithine)-aspartic acid-glutamic acid, (N-alkylated ornithine)-(N-alkylated ornithine)-aspartic acid-arginine, (N-alkylated ornithine)-(N-alkylated ornithine)-aspartic acid-histidine, (N-alkylated ornithine)-(N-alkylated ornithine)-aspartic acid-lysine, (N-alkylated ornithine)-(N-alkylated ornithine)-glutamic acid-arginine, (N-alkylated ornithine)-(N-alkylated ornithine)-glutamic acid-histidine, (N-alkylated ornithine)-(N-alkylated ornithine)-glutamic acid-lysine, (N-alkylated ornithine)-(N-alkylated ornithine)-arginine-histidine, (N-alkylated ornithine)-(N-alkylated ornithine)-arginine-lysine, or (N-alkylated ornithine)-(N-alkylated ornithine)-histidine-lysine (wherein, "-" denotes an amide bond).

According to yet another preferable embodiment, the present invention relates to a peptide analogue or a pharmaceutically acceptable salt thereof having a structure of the following Chemical Formula 4.

[Chemical Formula 4]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine,
n is an integer of 3 to 7, and
m is an integer of 1 to 5.

More specifically, the peptide analogue of the Chemical Formula 4 may be preferably a tetrapeptide wherein N-alkylated lysine or N-alkylated ornithine independently or simultaneously forms an amide bond to the side chain of N-alkylated lysine or N-alkylated ornithine, and aspartic acid, glutamic acid, arginine, histidine or lysine is amide bonded thereto; and specific examples thereof may include (N-alkylated lysine amide-bonded to side chain)-(N-alkylated lysine)-aspartic acid-glutamic acid, (N-alkylated lysine amide-bonded to side chain)-(N-alkylated lysine)-aspartic acid-arginine, (N-alkylated lysine amide-bonded to side chain)-(N-alkylated lysine)-aspartic acid-histidine, (N-alkylated lysine amide-bonded to side chain)-(N-alkylated lysine)-aspartic acid-lysine, (N-alkylated lysine amide-bonded to side chain)-(N-alkylated lysine)-glutamic acid-arginine, (N-alkylated lysine amide-bonded to side chain)-(N-alkylated lysine)-glutamic acid-histidine, (N-alkylated lysine amide-bonded to side chain)-(N-alkylated lysine)-glutamic acid-lysine, (N-alkylated lysine amide-bonded to side chain)-(N-alkylated lysine)-arginine-histidine, (N-alkylated lysine amide-bonded to side chain)-(N-alkylated lysine)-arginine-lysine, (N-alkylated lysine amide-bonded to side chain)-(N-alkylated lysine)-histidine-lysine, (N-alkylated ornithine amide-bonded to side chain)-(N-alkylated ornithine)-aspartic acid-glutamic acid, (N-alkylated ornithine amide-bonded to side chain)-(N-alkylated ornithine)-aspartic acid-arginine, (N-alkylated ornithine amide-bonded to side chain)-(N-alkylated ornithine)-aspartic acid-histidine, (N-alkylated ornithine amide-bonded to side chain)-(N-alkylated ornithine)-aspartic acid-lysine, (N-alkylated ornithine amide-bonded to side chain)-(N-alkylated ornithine)-glutamic acid-arginine, (N-alkylated ornithine amide-bonded to side chain)-(N-alkylated ornithine)-glutamic acid-histidine, (N-alkylated ornithine amide-bonded to side chain)-(N- alkylated ornithine)-glutamic acid-lysine, (N-alkylated ornithine amide-bonded to side chain)-(N-alkylated ornithine)-arginine-histidine, (N-alkylated ornithine amide-bonded to side chain)-(N-alkylated ornithine)-arginine-lysine, (N-alkylated ornithine amide-bonded to side chain)-(N-alkylated ornithine)-histidine-lysine (wherein, "-" denotes an amide bond).

According to still another preferable embodiment, the present invention relates to a peptide analogue or a pharmaceutically acceptable salt thereof having a structure of the following Chemical Formula 5.

[Chemical Formula 5]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine, n is an integer of 3 to 7, and
m is an integer of 1 to 5.

More specifically, the peptide analogue of the Chemical Formula 5 may be preferably a pentapeptide wherein N-alkylated lysine or N-alkylated ornithine forms amide bonds simultaneously to the N-terminal and the side chain of lysine or ornithine, and aspartic acid, glutamic acid, arginine, histidine or lysine are amide bonded thereto; and specific examples thereof may include (N-alkylated lysine)$_2$-lysine-aspartic acid-glutamic acid, (N-alkylated lysine)$_2$-lysine-aspartic acid-arginine, (N-alkylated lysine)$_2$-lysine-aspartic acid-histidine, (N-alkylated lysine)$_2$-lysine-aspartic acid-lysine, (N-alkylated lysine)$_2$-lysine-glutamic acid-arginine, (N-alkylated lysine)$_2$-lysine-glutamic acid-histidine, (N-alkylated lysine)$_2$-lysine-glutamic acid-lysine, (N-alkylated lysine)$_2$-lysine-arginine-histidine, (N-alkylated lysine)$_2$-lysine-arginine-lysine, (N-alkylated lysine)$_2$-lysine-histidine-lysine, (N-alkylated ornithine)$_2$-ornithine-aspartic acid-glutamic acid, (N-alkylated ornithine)$_2$-ornithine-aspartic acid-arginine, (N-alkylated ornithine)$_2$-ornithine-aspartic acid-histidine, (N-alkylated ornithine)$_2$-ornithine-aspartic acid-lysine, (N-alkylated ornithine)$_2$-ornithine-glutamic acid-arginine, (N-alkylated ornithine)$_2$-ornithine-glutamic acid-histidine, (N-alkylated ornithine)$_2$-ornithine-glutamic acid-lysine, (N-alkylated ornithine)$_2$-ornithine-arginine-histidine, (N-alkylated ornithine)$_2$-ornithine-arginine-lysine, or (N-alkylated ornithine)$_2$-ornithine-histidine-lysine.

Wherein, "-" denotes an amide bond; "(N-alkylated lysine)$_2$-lysine" denotes that N-alkylated lysines respectively form amide bonds to the N-terminal and the side chain of lysine; and "(N-alkylated ornithine)$_2$-ornithine" denotes that N-alkylated ornithines respectively form amide bonds to the N-terminal and the side chain of ornithine.

In order to develop the peptide analogues of the present invention, the inventors assiduously observed the structure of the materials with hydrophilic residues and moisture retention capacity. As the result, a carboxylic acid could be derived as a reactive residue commonly existing in amino acid, pyrrolidone carboxylic acid, aminohexanoic acid, and the like, which are known to have excellent moisturizing effect. And, as the result of analyzing the composition of the fragments with excellent moisturizing effect among the decomposition product of silk peptide, it was confirmed that most of them comprise a carboxylic acid group in di- or tripeptide. Thus, the peptide analogues of the Chemical Formula 1 to Chemical Formula 5, which include di- or tripeptide and sufficient carboxylic acids and have maximized moisturizing effect, could be developed.

And, the present invention includes pharmaceutically acceptable salts of the peptide analogues of the Chemical Formula 1 to Chemical Formula 5.

As used herein, 'pharmaceutically acceptable salts' include salts derived from inorganic acid, organic acid or base. Examples of the suitable acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzene sulfonic acid, and the like. The salts derived from suitable base may include alkali metal, alkali earth metal such as magnesium, and ammonium, and the like.

According to another embodiment, the present invention relates to a method for synthesizing the novel peptide analogues.

The peptide analogues or pharmaceutically salts thereof may be prepared using techniques known in the art. Representative synthesis methods are summarized in the following Equation 1 to Equation 4, but are not limited thereto, and may be appropriately modified by one of ordinary knowledge in the art.

[Equation 1]

m = 3-4
R, R' = amino acid side chain

[Equation 3]

[Equation 2]

m = 3-4
R, R' = amino acid side chain m = 3-4
R, R' = amino acid side chain

[Equation 4]

-continued m = 3-4
R, R' = amino acid side chain

In the specific examples of the present invention, peptide analogues with moisturizing effect were synthesized using a Fmoc-chemistry synthesis method according to solid phase peptide synthesis (SPPS) and a solution chemistry synthesis method.

According to the solid phase peptide synthesis method, a peptide is synthesized by 1) loading protected amino acid on a resin; 2) removing the protection group of the amino acid; 3) inducing a coupling reaction of the amino acid; 4) confirming the reaction (for example, Kaiser test); 5) removing the resin and the protection group; and 6) solidifying peptide, and finally, a compound was synthesized by an N-alkylation reaction in a solution phase.

Hereinafter, the synthesis method will be explained in more detail according each step.

In the step 1), amino acid is loaded on a resin. As the resin, hydroxyl resin Wang (HMP; 4-Hydroxymethylphenoxy), and the like may be used, and the resin is swollen by adding an appropriate solvent. As the solvent, MC (methylenechloride) may be used, but not limited thereto. Next, the solvent is removed under reduced pressure, and protected amino acid dissolved in an appropriate solvent and a mixed solution of DIC (diisopropylcarbodiimide) and DMAP (4-dimethylaminopyridine) are added to a container and reacted. As the solvent, for example, DMF (dimethylformamide) may be used, and as the protection group of the amino acid, Fmoc (9-Fluorenylmethoxycarbonyl) may be used, but they are not limited thereto.

In the step 2), the protection group of amino acid is removed. The removal of the protection group of amino acid may be conducted according to a method commonly known in the art, and in specific examples of the invention, the amino acid solution loaded on a resin is removed under reduced pressure and washed, and then, reacted with a DMF solution diluted with piperidine to remove a protection group.

In the step 3), a coupling reaction of amino acid is induced. The amino acid coupling reaction may be conducted by methods commonly known in the art, for example, a HOBt-DCC (N-hydroxybenzotriazole-dicyclohexylcarodiimide dicyclohexylcarbodiimide) method or a HOBt-DIC (N-hydroxybenzotriazole-diisopropylcarbodiimide) method, and the like (Wang C. Chan, Perter D. white, "Fmoc solid phase peptide synthesis", Oxford). Besides, the reaction may be progressed using a coupling reagent such as N,N'-dicyclohexylcarbodiimide (DCC), N,N'-diisopropylcarbodiimide (DIC), O-benzotriazole-1-yl-N,N,N',N'-tetramethyluroniumhexafluorophosphate (HBTU), benzo-triazole-1-yloxytris (dimethylamino)phosphonium hexafluorophosphate (PyBOP), benzo-triazole-1-yloxytris(dimethylamino)phosphonium hexafluorophosphate (BOP), [O-(7-azabenzotriazole-1-yl)-N,N,N',N'-tetramethyluroniumhexafluorophosphate] (HATU), 1H-hydroxybenzotriazole (HOBO, 1H-hydroxy-7-azabenzotriazole (HOAt), and the like, and the reaction may be progressed by adding organic base such as trifluoroacetic acid (TFA), diisopropylethylamine (DIPEA), N methylmorpholin N methylmorpholine (NMM), and the like according to the coupling reagent, but not limited thereto.

In the step 4), it is confirmed whether or not the reaction has occurred. For example, in specific examples of the invention, Kaiser test (E. Kaiser et al., *Anal. Biochem.* (1970) 34, 595)) is used to confirm the amino acid coupling reaction. The Kaiser test is a qualitative method of confirming the existence of the functional group of primary amine by difference in color change using ninhydrin. Specifically, after the amino acid coupling reaction, 2~3 drops of Kaiser Test solutions are added to the small amount of washed resin, and then, color change of resin is observed for a specific time, and if there is no color change of resin, it is considered that the coupling reaction has been progressed, and the subsequent reaction is conducted, and if resin becomes blue, it is considered that unreacted parts remain, and the amino acid coupling reaction may be conducted again.

In the step 5), the resin and the protection group are removed. The steps 3) to 5) are repeated to remove the resin in the synthesized peptide, and the amino acid side chain is deprotected. The removal of resin and amino acid protection group may be conducted by methods commonly known in the art, and in specific examples of the invention, a peptide solution is obtained by adding a cleavage cocktail solution consisting of TFA (trifluoroacetic acid), TIS (triisopropylsilane), thioanisole, $H_2O$, and EDT (ethanedithiol). The composition of the solution may be appropriately modified by one of ordinary knowledge in the art according to experiment conditions.

In the step 6), the peptide is solidified. For example, excessive amount of a diethylether solvent may be added to produce precipitated solid, but not limited thereto. If peptide is synthesized by the above steps, an N-alkylation of the peptide may be conducted to introduce an alkyl group at a desired amino group. In the present invention, since it is preferable to alkylate $-(CH_2)_mC(=O)OH$ at the amino group of the peptide, bromoacetic acid, and the like capable of providing an alkyl group as an alkylation agent may be used, but not limited thereto.

The peptide analogues and pharmaceutically acceptable salts thereof according to the present invention do not cause side effects and stickyness to skin, and form a long-lasting moisturizing film on the skin surface, thereby manifesting excellent moisturizing effect. Specifically, in specific examples of the invention, the peptide analogues according to the present invention exhibited about 20-30% improved moisture retention capacity compared to buffer solution control (FIG. 1), and the formulations comprising the peptide analogues according to the present invention exhibited statistically significantly higher skin electrical conductivity compared to non-added formulation after 8 hours, and exhibited excellent skin moisture content increasing effect even 12 hours after coated on the skin (FIG. 2).

Thus, according to yet another embodiment, the present invention relates to a moisturizing composition comprising at least one selected from the group consisting of the peptide analogue or the pharmaceutically acceptable salt thereof according to the present invention. The moisturizing composition comprising the peptide analogue or the pharmaceutically acceptable salt thereof according to the present invention includes both a cosmetic composition and a pharmaceutical composition according to the use and desired effect.

According to preferable embodiment, the present invention relates to a moisturizing cosmetic composition comprising at least one selected from the group consisting of the peptide analogue or the pharmaceutically acceptable salt thereof according to the present invention.

If used as a moisturizing cosmetic composition, the composition may be applied to skin, scalp or hair, and may be used for prevention of skin aging, anti-wrinkle, and improvement of skin roughness.

According to another preferable embodiment, the present invention relates to a method for moisturizing skin, comprising administering at least one selected from the group consisting of the peptide analogue or the pharmaceutically acceptable salt thereof according to the present invention to an individual.

According to another preferable embodiment, the present invention relates to a pharmaceutical composition for prevention or treatment of xeroderma, comprising at least one selected from the group consisting of the peptide analogue or the pharmaceutically acceptable salt thereof according to the present invention.

If used as a pharmaceutical composition, the composition may be used for prevention or treatment of xeroderma such as skin fissure, erythema, pruritus, psoriasis or atopic dermatitis.

According to another preferable embodiment, the present invention relates to a method for treating xeroderma, comprising administering at least one selected from the group consisting of the peptide analogue or the pharmaceutically acceptable salt thereof according to the present invention to an individual.

Since the peptide analogues included in the moisturizing composition of the present invention may manifest effect if it forms a moisturizing film on the skin surface without being absorbed in the body or skin, the molecular weight range is not specifically limited, but those having weight average molecular weight of 100 to 10,000, preferably 100 to 2,000 may be commonly used.

The content of the peptide analogues included in the moisturizing composition of the present invention may be appropriately controlled according to the use, applied form, purpose and desired effect of the composition, and considering the effect compared to the content, it may be, for example, 0.0001 to 99 wt %, preferably 0.01 to 50 wt %, more preferably 0.01 to 10 wt %, most preferably 0.01 to 1 wt %, based on the total weight of the composition. If the content of the composition is less than the above range, substantial moisturizing effect may not be obtained, and if it is greater than the above range, stability of the formulation may be lowered due to the high moisturizing effect of the raw material, and the obtained effect may be insignificant compared to the content, and thus, it may not be economical.

The moisturizing composition of the present invention may be administered orally, transdermally, subcutaneously, or intravenously, and preferably, it may be administered orally or transdermally, more preferably subcutaneously.

The cosmetic composition refers to a composition that is transdermally applied to skin, scalp or hair, and may be used for preparation of cosmetic products such as basic cosmetics, makeup cosmetics, body products, shaving products, hair products, and the like, and it may be formulated in the form of solid medicine, spray, suspension, emulsion, cream, gel, foam, and the like, but the form is not specifically limited.

And, the pharmaceutical composition manifests the effects of prevention and/or treatment of diseases caused by xeroderma and/or xerasia by moisturization, it may be primarily administered orally or transdermally, and it may be formulated in the form of solid, spray, suspension, emulsion, cream, gel, and the like, but the form is not specifically limited. The diseases caused by xerosis includes skin fissures, erythema, pruritus, psoriasis, atopic dermatitis, and the like. Thus, the pharmaceutical composition of the present invention may be a composition for prevention and/or treatment of diseases caused by xerosis selected from the group consisting of skin fissures, erythema, pruritus, psoriasis, atopic dermatitis, and the like.

Since the cosmetic composition and the pharmaceutical composition and with excellent moisturizing effect according to the present invention may also exhibit the effects of preventing skin aging, anti-wrinkle, and improving skin roughness, and the like due to the excellent moisturizing effect, it may exhibit excellent effect for improvement of skin condition and prevention of worsening of skin condition.

The cosmetic composition and the pharmaceutical composition according to the present invention may further comprise all kinds of ingredients that can be used for formulation, for example, a flavoring agent, a pigment, a germicide, an antioxidant, an antiseptic, a humectant, a thickener, an excipients, a diluent, an inorganic salt and synthetic polymer material, and the like, in addition to the active ingredients, and the kind and the content may be appropriately controlled according to the use and purpose of the final product.

And, the composition of the present invention may comprise solvents that are commonly included in the applied form, and for example, may comprise at least one solvent selected from the group consisting of ethanol, glycerin, butyleneglycol, propyleneglycol, polyethyleneglycol, 1,2,4-butanetriol, sorbitol ester, 1,2,6-hexanetriol, benzyl alcohol, isopropanol, butanediol, diethyleneglycol monoethylether, dimethyl isosorbide, N-methyl-2-pyrrolidone, propylene carbonate, Glycereth-26, Methyl Gluceth-20, isocetyl myristate, isocetyl octanoate, octyl dodecyl myristate, octyl dodecanol, isostearyl isostearate, cetyl octanoate and neopentyl glycol dicaprate. When the composition of the present invention is prepared using the solvent, although solubility of the compound in the solvent slightly differs according to the kind of the compound or the mixing ratio of the solvent, one of ordinary knowledge in the art could appropriately select the kind and the use amount of the solvent according the properties of the product.

And, the composition of the present invention may comprise various materials for increasing transdermal permeation. For example, it may include laurocapram derivatives and ester derivatives of oleic acid, monooleate, adapalene, tretinoin, retinaldehyde, tazarotene, salicylic acid, azelaic acid, glycolic acid, ethoxydiglycolide, Tween 80, lecithin organogel, and the like. And, to afford additional functions, the composition of the present invention may further comprise auxiliary ingredients such as a cosurfactant, a surfactant, an anti-dandruff, a keratin softener, a blood flow stimulant, a cell activator, a refresher, a humectant, an antioxidant, a pH regulator, purified water, and the like, within the range that does not have a bad influence on the moisturizing effect of the composition, and it may comprise additives such as a flavoring agent, pigment, antiseptics, excipients, and the like according to the applied form.

Hereinafter, the present invention will be explained with reference to the following Examples. However, these examples are only to illustrate the invention, and the present invention is not limited thereto.

Example 1

Preparation of Peptide Analogues

In the present invention, total 24 peptides were obtained by solid phase synthesis using Fmoc (9-luorenylmethoxycarbonyl) as an Nα-amino acid protection group and an N-alkylation process, and the specific examples are as follows.

First, the amount of 1 mmol of hydroxyl resin, Wang (HMP; 4-Hydroxymethylphenoxy) resin (1.1 mmol/g, Novabiochem Corporation) was measured and put in a reactor, and then, MC 30 ml was added, and the resin was swollen for 10 minutes. The solvent was removed under reduced pressure, a mixture of Fmoc-lysine or Fmoc-ornithine (4 eq.), DIC (2 eq.; Diisopropylcarbodiimide) & DMAP (0.1 eq.; 4-Dimethylaminopyridine) dissolved in a DMF solvent was added to the reactor, and reacted for 4 hours. And then, the amino acid solution loaded on the Wang resin was removed under reduced pressure, and the resin was washed with DMF and MC respectively 30 ml×5 times. The resin loaded with Fmoc-amino acid was reacted with a DMF solution diluted with 20% (v/v) piperidine for 10 minutes to deprotect, and then, washed with DMF and MC respectively 30 ml×5 times. And then, to the Fmoc protection group-removed resin, a coupling solution of Fmoc-amino acid (4 eq.), DIC (4 eq.; Diisopropylcarbodiimide), HOBt (4 eq.; N-hydroxybenzotriazole) dissolved in a DMF solvent was added, and reacted at room temperature for 4 hours to induce an amino acid coupling reaction. After the amino acid coupling reaction, a Kaiser test solutions A, B, C[reagent A: ninhydrin (5 g) in ethanol (100 ml), reagent B: phenol (80 g) in ethanol (20 ml), reagent C, 0.1M KCN (2 ml) in pyridine (98 ml)] were added 2-3 drops to the small amount of washed resin, and then, color change of the resin was observed for 10 minutes while maintaining the temperature at 100° C. If there is no color change of the resin, it was considered that a coupling reaction progressed, and the subsequent reaction was conducted, and if the resin appears in blue, it was considered that unreacted parts remained, and the amino acid coupling reaction was conducted again.

The peptide synthesized by the above processes was removed from the resin, and to deprotect the amino acid side chain, a mixture of TFA (trifluoroacetic acid), TIS (triisopropylsilane), thioanisole, H$_2$O, EDT (ethanedithiol) was added in the ratio of 90:2.5:2.5:2.5:2.5 to produce precipitated solid, and the precipitate was centrifuged to remove the filtrate of TFA, TIS, thioanisole, H$_2$O, EDT, and the like, which was repeated 3 or more times to obtained solidified peptide.

Next, 1 mmol of the peptide obtained through the solidification step was dissolved in water, and then, a 1N NaOH (4 eq.) solution was slowly added. The mixture was agitated at room temperature for 10 minutes, cooled to 0° C., and then, bromoacetic acid (4~8 eq.) was slowly added. After agitating for 10 minutes in a cooled state, an ice bath was removed, and the mixture was reacted at room temperature for 12 hours. After the reaction, the mixture was further agitated at 60° C. for 4 hours, and then, the reaction was completed, EA was added to wash the aqueous layer 3~4 times, and N-alkylated peptide was obtained through reverse phase chromatography.

For peptides II-1, II-2, II-3, II-4, II-9, II-10, II-11, II-12, specific synthesis methods are as shown in the following Equation 2.

[Equation 2]

m = 3-4
R, R' = amino acid side chain

For peptides II-5, II-6, II-13, II-14, specific synthesis methods are as shown in the following Equation 3.

[Equation 3]

For peptides II-7, II-8, II-15, II-16, specific synthesis methods are as shown in the following Equation 4.

[Equation 4]

m = 3-4
R, R' = amino acid side chain

The purification conditions and the molecular weights of the peptides obtained by the above process are as follows.

Example 1-1

Preparation of Peptide I-1

Rt=11.25 minutes (various concentration gradients over 30 minutes from 5 to 100% acetonitrile/water containing 0.01% TFA); MS (ESI) m/e, [M+H]+=479

(Hereinafter, the unit % denotes % (v/v) unless otherwise stated).

Example 1-2

Preparation of Peptide I-2

Rt=10.65 minutes (various concentration gradients over 30 minutes from 5 to 100% acetonitrile/water containing 0.01% TFA); MS (ESI) m/e, [M+H]+=595

Example 1-3

Preparation of Peptide I-3

Rt=10.57 minutes (various concentration gradients over 30 minutes from 5 to 100% acetonitrile/water containing 0.01% TFA); MS (ESI) m/e, [M+H]+=595

Example 1-4

Preparation of Peptide I-4

Rt=10.38 minutes (various concentration gradients over 30 minutes from 5 to 100% acetonitrile/water containing 0.01% TFA); MS (ESI) m/e, [M+H]+=825

Example 1-5

Preparation of Peptide I-5

Rt=12.87 minutes (various concentration gradients over 30 minutes from 5 to 100% acetonitrile/water containing 0.01% TFA); MS (ESI) m/e, [M+H]+=507

Example 1-6

Preparation of Peptide I-6

Rt=11.25 minutes (various concentration gradients over 30 minutes from 5 to 100% acetonitrile/water containing 0.01% TFA); MS (ESI) m/e, [M+H]+=623

Example 1-7

Preparation of Peptide I-7

Rt=10.75 minutes (various concentration gradients over 30 minutes from 5 to 100% acetonitrile/water containing 0.01% TFA); MS (ESI) m/e, [M+H]+=623

Example 1-8

Preparation of Peptide I-8

Rt=10.58 minutes (various concentration gradients over 30 minutes from 5 to 100% acetonitrile/water containing 0.01% TFA); MS (ESI) m/e, [M+H]+=867

Example 1-9

Preparation of Peptide II-1

Rt=15.25 minutes (various concentration gradients over 30 minutes from 5 to 100% acetonitrile/water containing 0.01% TFA); MS (ESI) m/e, [M+H]+=723

Example 1-10

Preparation of Peptide II-2

Rt=14.87 minutes (various concentration gradients over 30 minutes from 5 to 100% acetonitrile/water containing 0.01% TFA); MS (ESI) m/e, [M+H]+=772

Example 1-11

Preparation of Peptide II-3

Rt=14.75 minutes (various concentration gradients over 30 minutes from 5 to 100% acetonitrile/water containing 0.01% TFA); MS (ESI) m/e, [M+H]+=839

Example 1-12

Preparation of Peptide II-4

Rt=15.45 minutes (various concentration gradients over 30 minutes from 5 to 100% acetonitrile/water containing 0.01% TFA); MS (ESI) m/e, [M+H]+=888

Example 1-13

Preparation of Peptide II-5

Rt=15.64 minutes (various concentration gradients over 30 minutes from 5 to 100% acetonitrile/water containing 0.01% TFA); MS (ESI) m/e, [M+H]+=839

Example 1-14

Preparation of Peptide II-6

Rt=14.65 minutes (various concentration gradients over 30 minutes from 5 to 100% acetonitrile/water containing 0.01% TFA); MS (ESI) m/e, [M+H]+=888

Example 1-15

Preparation of Peptide II-7

Rt=16.29 minutes (various concentration gradients over 30 minutes from 5 to 100% acetonitrile/water containing 0.01% TFA); MS (ESI) m/e, [M+H]+=1070

Example 1-16

Preparation of Peptide II-8

Rt=16.35 minutes (various concentration gradients over 30 minutes from 5 to 100% acetonitrile/water containing 0.01% TFA); MS (ESI) m/e, [M+H]+=1119

Example 1-17

Preparation of Peptide II-9

Rt=15.25 minutes (various concentration gradients over 30 minutes from 5 to 100% acetonitrile/water containing 0.01% TFA); MS (ESI) m/e, [M+H]+=751

Example 1-18

Preparation of Peptide II-10

Rt=14.55 minute (various concentration gradients over 30 minutes from 5 to 100% acetonitrile/water containing 0.01% TFA); MS (ESI) m/e, [M+H]+=801

Example 1-19

Preparation of Peptide II-11

Rt=15.55 minutes (various concentration gradients over 30 minutes from 5 to 100% acetonitrile/water containing 0.01% TFA); MS (ESI) m/e, [M+H]+=867

Example 1-20

Preparation of Peptide II-12

Rt=14.75 minutes (various concentration gradients over 30 minutes from 5 to 100% acetonitrile/water containing 0.01% TFA); MS (ESI) m/e, [M+H]+=916

Example 1-21

Preparation of Peptide II-13

Rt=14.39 minutes (various concentration gradients over 30 minutes from 5 to 100% acetonitrile/water containing 0.01% TFA); MS (ESI) m/e, [M+H]+=867

Example 1-22

Preparation of Peptide II-14

Rt=14.31 minutes (various concentration gradients over 30 minutes from 5 to 100% acetonitrile/water containing 0.01% TFA); MS (ESI) m/e, [M+H]+=916

Example 1-23

Preparation of Peptide II-15

Rt=16.18 minutes (various concentration gradients over 30 minutes from 5 to 100% acetonitrile/water containing 0.01% TFA); MS (ESI) m/e, [M+H]+=1112

Example 1-24

Preparation of Peptide II-16

Rt=16.75 minutes (various concentration gradients over 30 minutes from 5 to 100% acetonitrile/water containing 0.01% TFA); MS (ESI) m/e, [M+H]+=1161

The following Table 1 shows the list of synthesized peptides, wherein asp denotes aspartic acid, glu denotes glutamic acid, his denotes histidine, and arg denotes arginine. The peptide analogues of the Table 1 include peptide of the following Chemical Formula 1 as the basic structure.

[Chemical Formula I]

TABLE 1

| No. | n | $X_1, X_2$ | $Y_1, Y_2$ | When $X_1$ & $Y_1$ are W, $R_{1-4}$ | $Z_1$ | $Z_2$ | Mass molecular weight Theoretical value | Mass molecular weight Experimental value |
|---|---|---|---|---|---|---|---|---|
| I-1  | 3 | W, —H          | —CH$_2$COOH    | $R_{1,2}$ = CH$_2$COOH | —O  | —H  | 478.45  | 479.38  |
| I-2  | 3 | W, —H          | —CH$_2$COOH    | —CH$_2$COOH            | —O  | —H  | 594.52  | 595.46  |
| I-3  | 3 | —CH$_2$COOH    | W, —H          | —CH$_2$COOH            | —O  | —H  | 594.52  | 595.48  |
| I-4  | 3 | W, —H          | W, —H          | —CH$_2$COOH            | —O  | —H  | 824.74  | 825.84  |
| I-5  | 4 | W, —H          | —CH$_2$COOH    | $R_{1,2}$ = CH$_2$COOH | —O  | —H  | 506.50  | 507.48  |
| I-6  | 4 | W, —H          | —CH$_2$COOH    | —CH$_2$COOH            | —O  | —H  | 622.58  | 623.35  |
| I-7  | 4 | —CH$_2$COOH    | W, —H          | —CH$_2$COOH            | —O  | —H  | 622.58  | 623.88  |
| I-8  | 4 | W, —H          | W, —H          | —CH$_2$COOH            | —O  | —H  | 866.82  | 867.72  |
| II-1 | 3 | W, —H          | —CH$_2$COOH    | $R_{1,2}$ = CH$_2$COOH | Asp | Glu | 722.65  | 723.48  |
| II-2 | 3 | W, —H          | —CH$_2$COOH    | $R_{1,2}$ = CH$_2$COOH | His | Arg | 771.78  | 772.86  |
| II-3 | 3 | W, —H          | —CH$_2$COOH    | —CH$_2$COOH            | Asp | Glu | 838.72  | 839.65  |
| II-4 | 3 | W, —H          | —CH$_2$COOH    | —CH$_2$COOH            | His | Arg | 887.85  | 888.79  |
| II-5 | 3 | —CH$_2$COOH    | W, —H          | —CH$_2$COOH            | Asp | Glu | 838.72  | 839.65  |
| II-6 | 3 | —CH$_2$COOH    | W, —H          | —CH$_2$COOH            | His | Arg | 887.85  | 888.35  |
| II-7 | 3 | W, —H          | W, —H          | —CH$_2$COOH            | Asp | Glu | 1068.94 | 1069.74 |
| II-8 | 3 | W, —H          | W, —H          | —CH$_2$COOH            | His | Arg | 1118.07 | 1119.18 |
| II-9 | 4 | W, —H          | —CH$_2$COOH    | $R_{1,2}$ = CH$_2$COOH | Asp | Glu | 750.71  | 751.68  |
| II-10| 4 | W, —H          | —CH$_2$COOH    | $R_{1,2}$ = CH$_2$COOH | His | Arg | 799.83  | 800.75  |
| II-11| 4 | W, —H          | —CH$_2$COOH    | —CH$_2$COOH            | Asp | Glu | 866.78  | 867.58  |
| II-12| 4 | W, —H          | —CH$_2$COOH    | —CH$_2$COOH            | His | Arg | 915.90  | 916.79  |
| II-13| 4 | —CH$_2$COOH    | W, —H          | —CH$_2$COOH            | Asp | Glu | 866.78  | 867.68  |
| II-14| 4 | —CH$_2$COOH    | W, —H          | —CH$_2$COOH            | His | Arg | 915.90  | 916.78  |
| II-15| 4 | W, —H          | W, —H          | —CH$_2$COOH            | Asp | Glu | 1111.02 | 1112.09 |
| II-16| 4 | W, —H          | W, —H          | —CH$_2$COOH            | His | Arg | 1160.15 | 1161.35 |

Example 2

Measurement of Moisture Retention Capacities of Peptide Analogues

The peptide analogues I-5, I-6, I-7 and I-8 synthesized by the above synthesis methods were dissolved in a glycerin 5% solution to 1% (w/v), a cotton pad was dipped in each 1 ml of the obtained solutions, and change in weight was measured at an appropriate time interval under 24° C., 45~50% RH (relative humidity).

The obtained results are shown in the following Table 2 and FIG. 1.

TABLE 2

| The amount of evaporated moisture (mg) | 5 minutes | 15 minutes | 30 minutes | 60 minutes | 120 minutes | 240 minutes | 360 minutes | Moisturizing capacity |
|---|---|---|---|---|---|---|---|---|
| Buffer | 15.7 | 57.1 | 91.5 | 153.9 | 264.7 | 395.7 | 499.5 | 100.0% |
| I-5 | 15.8 | 55.1 | 82.4 | 134.2 | 220.2 | 339.0 | 412.3 | 121.1% |
| I-6 | 19.1 | 69.2 | 81.1 | 124.8 | 211.1 | 303.2 | 398.1 | 125.4% |
| I-7 | 18.5 | 62.1 | 80.8 | 119.7 | 212.4 | 305.9 | 402.1 | 124.2% |
| I-8 | 19.0 | 56.0 | 79.4 | 111.9 | 204.9 | 298.6 | 385.0 | 129.7% |

Figure 1:
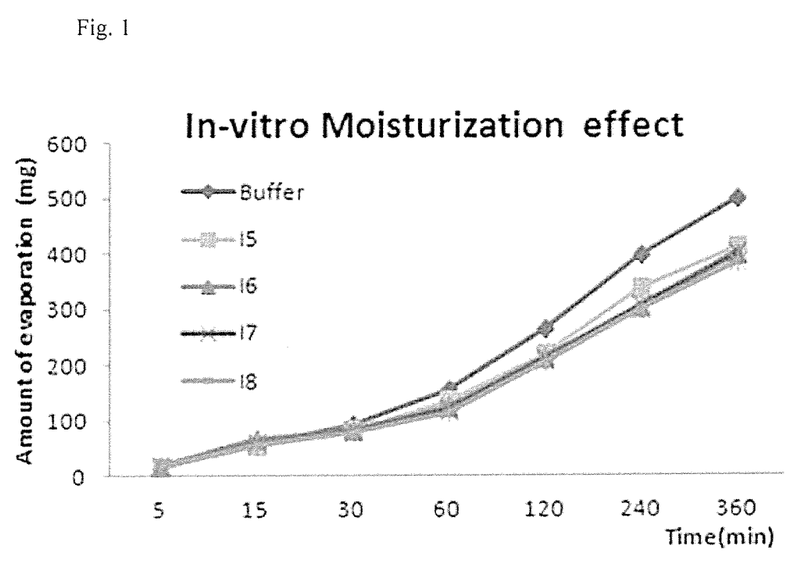
FIG. 1 shows the measurement results of moisture retention capacities of the peptide analogues according to the present invention.
Figure 2:
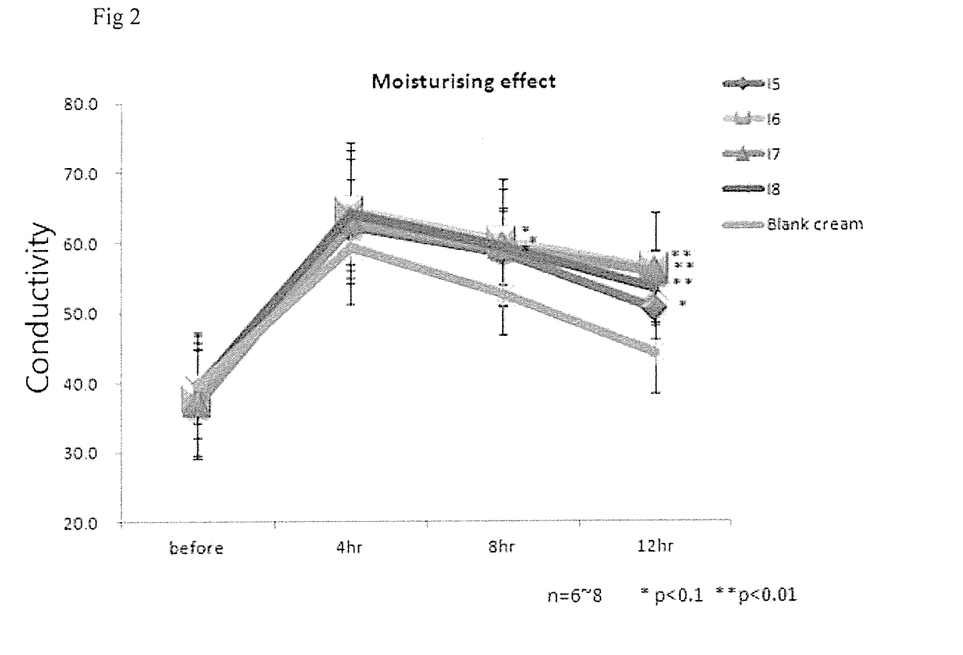
FIG. 2 show the measurement results of moisturizing effects of the peptide analogues according to the present invention.

As can be seen from the Table 2 and FIG. 1, the solutions comprising the peptide analogues I-5, I-6, I-7 and I-8 exhibit remarkable moisture retention capacities compared to buffer (5% glycerol solution), and particularly, the formulations comprising the I-6 and I-7 analogues exhibit about 20~30% improved moisture retention capacities. From the results, it was confirmed that the peptide analogues prepared so as to contain a large amount of carboxylic acid groups have excellent moisture retention capacities.

Example 3

Measurement of Moisturizing Effects of Peptide Analogues

To compare the moisturizing effects of the cosmetics comprising the peptide analogues I-5, I-6, I-7 and I-8, the moisturizing effects were measured in human skin with some combinations.

Specifically, 4 kinds of peptide analogues were respectively evenly mixed with Atopep cream manufactured by Genicos Co. Ltd. (a formulation containing cyclomethicone, betaine, sodium hyaluronic acid, glycerin, neopentylglycol dicaprate, squalane, propylene glycol, cetearyl alcohol, sorbitan stearate, PET-40 stearate, bees wax, stearic acid, lanolin wax, glycerin stearate, PEG-100 stearate, dimethicone, tocopheryl acetate, albutin, Coptis Japonica Root Extract, orus Bombycis Root Extract, aloevera leaf extract, carbomer, xanthan gum, methylparaben, fragrance, propylparaben, triethanolamine, EDTA 2sodium, imiazolidinyl urea) to 0.5% (w/v) to formulate into cream. And, a formulation that does not include peptide analogue was prepared as a control. And then, each composition was applied to the inside of the forearm of the subject in a fixed amount (0.03 g/16 m$^2$), and rubbed well. Before the application, 4 hours after the application, 8 hours after the application, and 12 hours after the application, electrical conductivity of the skin was measured using Corneometer CM825 (Courage & Khazaka Germany) to measure skin moisture content.

At the application, there was little difference in speadability and stickyness of the 4 formulations containing the peptide analogues with excellent moisturizing effect, and after the application, abnormal skin conditions such as erythema, pruritus, and the like did not appear.

And, as shown in FIG. 2, formulations comprising the peptide analogues with excellent moisturizing effect exhibited statistically significantly higher skin electrical conductivity compared to blank cream after 8 hours elapsed, and even 12 hours after applied to skin, they exhibited excellent skin moisture content increasing effects.

The invention claimed is:

1. A peptide analogue having the following Chemical Formula 2 or a pharmaceutically acceptable salt thereof:

[Chemical Formula 2]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine, n is an integer of 3 to 7, and m is an integer of 1 to 5.

2. A peptide analogue having the following Chemical Formula 3 or a pharmaceutically acceptable salt thereof:

[Chemical Formula 3]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine, n is an integer of 3 to 7, and m is an integer of 1 to 5.

3. A peptide analogue having the following Chemical Formula 4 or a pharmaceutically acceptable salt thereof:

[Chemical Formula 4]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine, n is an integer of 3 to 7, and m is an integer of 1 to 5.

4. A peptide analogue having the following Chemical Formula 5 or a pharmaceutically acceptable salt thereof:

[Chemical Formula 5]

wherein, R and R' are the same or different, and independently represent an amino acid side chain selected from the group consisting of alanine, aspartic acid, glutamic acid, glycine, histidine, lysine, asparagine, glutamine, arginine, tryptophan and tyrosine, n is an integer of 3 to 7, and m is an integer of 1 to 5.

5. A moisturizing cosmetic composition comprising at least one selected from the group consisting of the peptide analogue and the pharmaceutically acceptable salt thereof according to claim 1, 2, 3 or 4.

6. The moisturizing cosmetic composition according to claim 5, wherein the composition is applied to skin, scalp or hair.

7. The moisturizing cosmetic composition according to claim 5, wherein the composition is for prevention of skin aging, anti-wrinkle, or improvement of skin roughness.

8. A pharmaceutical composition for preventing or treating of xeroderma, comprising at least one selected from the group consisting of the peptide analogue and the pharmaceutically acceptable salt thereof according to claim 1, 2, 3 and or 4.

9. The pharmaceutical composition according to claim 8, wherein the xeroderma is skin fissure, erythema, pruritus, psoriasis or atopic dermatitis.

10. A peptide analogue having the following Chemical Formula 1 or a pharmaceutically acceptable salt thereof:

[Chemical Formula 1]

wherein wherein the peptide analogues are selected from peptide analogue No. 1-24 in the following table

| peptide analogue No. | n | $X_1$ | $X_2$ | $Y_1$ | $Y_2$ | W | $Z_1$ | $Z_2$ |
|---|---|---|---|---|---|---|---|---|
| 1 | 3 | W | —H | —$CH_2COOH$ | —$CH_2COOH$ | $R_1, R_2 =$ —$CH_2COOH$, $R_3, R_4 =$ —H | —O | —H |
| 2 | 3 | W | —H | —$CH_2COOH$ | —$CH_2COOH$ | $R_1, R_2, R_3, R_4 =$ —$CH_2COOH$ | —O | —H |
| 3 | 3 | —$CH_2COOH$ | —$CH_2COOH$ | W | —H | $R_1, R_2, R_3, R_4 =$ —$CH_2COOH$ | —O | —H |
| 4 | 3 | W | —H | W | —H | $R_1, R_2, R_3, R_4 =$ —$CH_2COOH$ | —O | —H |
| 5 | 4 | W | —H | —$CH_2COOH$ | —$CH_2COOH$ | $R_1, R_2 =$ —$CH_2COOH$, $R_3, R_4 =$ —H | —O | —H |

| peptide analogue No. | n | $X_1$ | $X_2$ | $Y_1$ | $Y_2$ | W | $Z_1$ | $Z_2$ |
|---|---|---|---|---|---|---|---|---|
| 6 | 4 | W | —H | —CH$_2$COOH | —CH$_2$COOH | $R_1, R_2, R_3, R_4 =$ —CH$_2$COOH | —O | —H |
| 7 | 4 | —CH$_2$COOH | —CH$_2$COOH | W | —H | $R_1, R_2, R_3, R_4 =$ —CH$_2$COOH | —O | —H |
| 8 | 4 | W | —H | W | —H | $R_1, R_2, R_3, R_4 =$ —CH$_2$COOH | —O | —H |
| 9 | 3 | W | —H | —CH$_2$COOH | —CH$_2$COOH | $R_1, R_2 =$ —CH$_2$COOH, $R_3, R_4 =$ —H | Asp | Glu |
| 10 | 3 | W | —H | —CH$_2$COOH | —CH$_2$COOH | $R_1, R_2 =$ —CH$_2$COOH, $R_3, R_4 =$ —H | His | Arg |
| 11 | 3 | W | —H | —CH$_2$COOH | —CH$_2$COOH | $R_1, R_2, R_3, R_4, =$ —CH$_2$COOH | Asp | Glu |
| 12 | 3 | W | —H | —CH$_2$COOH | —CH$_2$COOH | $R_1, R_2, R_3, R_4 =$ —CH$_2$COOH | His | Arg |
| 13 | 3 | —CH$_2$COOH | —CH$_2$COOH | W | —H | $R_1, R_2, R_3, R_4 =$ —CH$_2$COOH | Asp | Glu |
| 14 | 3 | —CH$_2$COOH | —CH$_2$COOH | W | —H | $R_1, R_2, R_3, R_4 =$ —CH$_2$COOH | His | Arg |
| 15 | 3 | W | —H | W | —H | $R_1, R_2, R_3, R_4 =$ —CH$_2$COOH | Asp | Glu |
| 16 | 3 | W | —H | W | —H | $R_1, R_2, R_3, R_4 =$ —CH$_2$COOH | His | Arg |
| 17 | 4 | W | —H | —CH$_2$COOH | —CH$_2$COOH | $R_1, R_2 =$ —CH$_2$COOH, $R_3, R_4 =$ —H | Asp | Glu |
| 18 | 4 | W | —H | —CH$_2$COOH | —CH$_2$COOH | $R_1, R_2 =$ —CH$_2$COOH, $R_3, R_4 =$ —H | His | Arg |
| 19 | 4 | W | —H | —CH$_2$COOH | —CH$_2$COOH | $R_1, R_2, R_3, R_4 =$ —CH$_2$COOH | Asp | Glu |
| 20 | 4 | W | —H | —CH$_2$COOH | —CH$_2$COOH | $R_1, R_2, R_3, R_4 =$ —CH$_2$COOH | His | Arg |
| 21 | 4 | —CH$_2$COOH | —CH$_2$COOH | W | —H | $R_1, R_2, R_3, R_4 =$ —CH$_2$COOH | Asp | Glu |
| 22 | 4 | —CH$_2$COOH | —CH$_2$COOH | W | —H | $R_1, R_2, R_3, R_4 =$ —CH$_2$COOH | His | Arg |
| 23 | 4 | W | —H | W | —H | $R_1, R_2, R_3, R_4 =$ —CH$_2$COOH | Asp | Glu |
| 24 | 4 | W | —H | W | —H | $R_1, R_2, R_3, R_4 =$ —CH$_2$COOH | His | Arg. |

11. A cosmetic composition comprising at least one selected from the group consisting of the peptide analogue and the pharmaceutically acceptable salt thereof according to claim 10.

12. A pharmaceutical composition comprising at least one selected from the group consisting of the peptide analogue and the pharmaceutically acceptable salt thereof according to claim 10.

* * * * *